(12) United States Patent
Hori et al.

(10) Patent No.: US 8,310,673 B2
(45) Date of Patent: Nov. 13, 2012

(54) LIGHT SOURCE

(75) Inventors: Masaru Hori, Nagoya (JP); Hiroyuki Kano, Nagoya (JP); Shoji Den, Yokohama (JP)

(73) Assignees: Nu Eco Engineering Co., Ltd., Nishikamo-Gun, Aichi (JP); Katagiri Engineering Co., Ltd., Yokohama-shi, Kanagawa (JP)

( * ) Notice: Subject to any disclaimer, the term of this patent is extended or adjusted under 35 U.S.C. 154(b) by 361 days.

(21) Appl. No.: 12/450,402

(22) PCT Filed: Mar. 24, 2008

(86) PCT No.: PCT/JP2008/055439
§ 371 (c)(1),
(2), (4) Date: Jan. 6, 2010

(87) PCT Pub. No.: WO2008/123196
PCT Pub. Date: Oct. 16, 2008

(65) Prior Publication Data
US 2010/0201978 A1    Aug. 12, 2010

(30) Foreign Application Priority Data

Mar. 26, 2007 (JP) ................................ 2007-080340

(51) Int. Cl.
*G01J 3/30* (2006.01)

(52) U.S. Cl. ...................................................... 356/316

(58) Field of Classification Search .................... 356/316
See application file for complete search history.

(56) References Cited

U.S. PATENT DOCUMENTS 4,833,322 A * 5/1989 Forster et al. ................. 250/288
5,021,646 A * 6/1991 Weinberger et al. ...... 250/227.11

* cited by examiner

*Primary Examiner* — Tarifur Chowdhury
*Assistant Examiner* — Abdullahi Nur
(74) *Attorney, Agent, or Firm* — McGinn IP Law Group, PLLC

(57) ABSTRACT

To provide a light source which realizes accurate determination of the particle density of a plasma atmosphere without disturbing the state of the plasma atmosphere.
The light source of the invention includes a tubular casing 12; a cooling medium passage 30 for causing a cooling medium to flow therethrough, the passage being provided along the inner wall of the casing; a lens 50 provided at a tip end of the casing; a first electrode 44 and a second electrode 45 which are provided in the casing and before the lens so as to be vertical to the axis of the casing and parallel to each other; and an insulating spacer 46 provided between the first electrode and the second electrode. The light source further includes a hole 47 axially penetrating the center portions of the first electrode, the insulating spacer, and the second electrode; and an electric discharge gas passage for introducing an electric discharge gas, along the inner wall of the cooling medium passage, to the back surface of the lens so that the electric discharge gas is reflected by the lens and flows through the hole.

12 Claims, 5 Drawing Sheets

LIGHT SOURCE

TECHNICAL FIELD

The present invention relates to a light source which is employed for determining the particle (atomic, molecular, etc.) density of a plasma atmosphere, and which, when in use, is inserted into a reaction chamber for forming a plasma.

BACKGROUND ART

When radicals of a raw material gas are generated, and a thin film of the raw material is formed on an object of interest, or an object of interest is etched by means of the thus-generated radicals, precise control of such a process requires determination of the atomic particle (e.g., radical) density of a plasma atmosphere for controlling formation of a plasma. For this purpose, such a plasma atmosphere is irradiated with light, and the atomic particle density of the plasma atmosphere is determined on the basis of light absorption features of the particles.

Determination of such a particle density requires a light source. For example, in a method disclosed in Patent Document 1, a light source is provided outside a reaction chamber. A plasma atmosphere is irradiated with light generated by electric discharge of the same gas as the plasma-forming gas from the outside of the reaction chamber, and the light is caused to pass through the plasma atmosphere. The light absorbed by atomic radicals is spectroscopically analyzed by means of a spectrometer provided outside the reaction chamber.

Patent Document 1: Japanese Patent Application Laid-Open (kokai) No. 2000-123996

DISCLOSURE OF THE INVENTION

Problems to be Solved by the Invention

However, in this method, difficulty is encountered in scanning the position at which light is applied in a plasma atmosphere, making it difficult to accurately determine the spatial distribution of particle density in the plasma atmosphere. In order to solve such a problem, a light source must be movably inserted into the plasma atmosphere, and light which has passed through the plasma atmosphere must be received by a probe which is movably provided so as to face the light source.

In view of the foregoing, an object of the present invention is to realize a light source which can be inserted into a plasma atmosphere without disturbing the state of the plasma atmosphere.

Means for Solving the Problems

In a first aspect of the present invention, there is provided a light source which, when in use, is inserted into a reaction chamber for generating a plasma atmosphere, and which is employed for determining the atom or molecule density of the plasma atmosphere through absorption spectroscopy, characterized by comprising a tubular casing; a cooling medium passage for causing a cooling medium to flow therethrough, the passage being provided along the wall of the casing; a lens provided at a tip end of the casing; a first electrode and a second electrode which are provided in the casing and before the lens so as to be vertical to the axis of the casing and parallel to each other; an insulating spacer provided between the first electrode and the second electrode; a hole axially penetrating the center portions of the first electrode, the insulating spacer, and the second electrode; and an electric discharge gas passage for introducing an electric discharge gas, along the inner wall of the cooling medium passage, to the back surface of the lens so that the electric discharge gas is reflected by the lens and flows through the hole.

In the present invention, the cooling medium passage may be placed in the side wall of the tubular casing. Alternatively, a tube may be inserted into the tubular casing so that a clearance is provided therebetween, and an end portion of the tubular casing may be sealed so that the clearance serves as a cooling medium passage. Alternatively, the cooling medium passage may be formed of a spiral tube provided outside or inside the tubular casing. The lens provided at the tip end of the tubular casing allows passage therethrough of light generated by electric discharge between the electrodes, and converts the light into parallel rays.

Plasma is a mass of charged particles or neutral particles, such as electrons, atomic radicals, molecular radicals, atomic ions, or molecular ions. The present invention is directed to a light source employed for determining the particle density of a plasma atmosphere, the target particles exhibiting specific absorption spectroscopic characteristics. The casing of the light source is formed of a rod-like tube, and light is output through a tip end of the casing. Since the diameter of the casing can be considerably reduced, when the light source is inserted into a plasma atmosphere, the particle density distribution profile in the plasma atmosphere can be accurately obtained without disturbing the state of the plasma.

A second aspect of the present invention is drawn to a specific embodiment of the light source according to the first aspect, wherein the light source has an electrically conductive spring for pressing the second electrode to the insulating spacer, and voltage is applied to the second electrode via the spring.

A third aspect of the present invention is drawn to a specific embodiment of the light source according to the first or second aspect, wherein the light source has a tubular electrode holder which is axially movably provided in the casing so as to support the first electrode, the insulating spacer, and the second electrode, and to be parallel to the axis of the casing, so that a clearance is provided between the outer wall of the electrode holder and the wall of the cooling medium passage; and the clearance and an internal space of the electrode holder serve as the electric discharge gas passage.

Effects of the Invention

According to the first aspect of the present invention, the cooling medium passage is cooled by a cooling medium, and an electric discharge gas which is supplied while coming into contact with the cooling medium passage is cooled. The electric discharge gas is supplied through the hole penetrating the first electrode and the second electrode, to thereby cool these electrodes. Through the cooling effect of the electric discharge gas on the electrodes, stable electric discharge is attained continuously. Thus, the light source attains reliable performance with a small variation in amount of light, and the accuracy in determining particle density is improved. The electric discharge gas is supplied to the back surface of the lens, and the electric discharge gas having been reflected by the lens flows toward the hole penetrating the electrodes. Since plasma particles of the electric discharge gas diffuse toward the back surface of the lens; i.e., the direction of flow of the plasma particles is opposite that of the electric discharge gas, the plasma particles are prevented from adhering to the back surface of the lens. Therefore, variation in light intensity can be prevented, and particle density can be accurately determined.

According to the second aspect of the present invention, since electricity is conducted to the second electrode via the spring, electric power can be effectively supplied to the second electrode. Even when the insulating spacer is replaced with one having a different thickness, reliable power supply can be attained, since the spring presses the second electrode to the insulating spacer. Since the second electrode is fixed to the insulating spacer by means of the spring, exchange of the insulating spacer is facilitated.

According to the third aspect of the present invention, the electrode holder is provided so as to support, at a tip end thereof, the first electrode, the insulating spacer, and the second electrode, and the electrode holder is movable with respect to the casing. The focal length of the lens differs with the wavelength of light emitted by electric discharge of the electric discharge gas (e.g., hydrogen, oxygen, or nitrogen). When the relative distance between the lens and the hole penetrating the electrodes is adjusted in response to a change in emission wavelength, rays of light having high parallelism can be obtained at an emission wavelength of interest, and the accuracy in determining particle density can be improved.

BEST MODES FOR CARRYING OUT THE INVENTION

A preferred embodiment of the present invention will next be described in detail. Technical matters that are necessary for carrying out the present invention but are not specifically referred to herein should be understood to be of design choice that those skilled in the art are recognized on the basis of conventional techniques. The present invention can be carried out on the basis of technical matters disclosed herein and techniques generally known to those skilled in the art.

The present invention will next be described with reference to an embodiment, but the invention is not limited to the embodiment. The present invention encompasses technical ideas understood from the embodiment.

Embodiment 1

Figure 1:
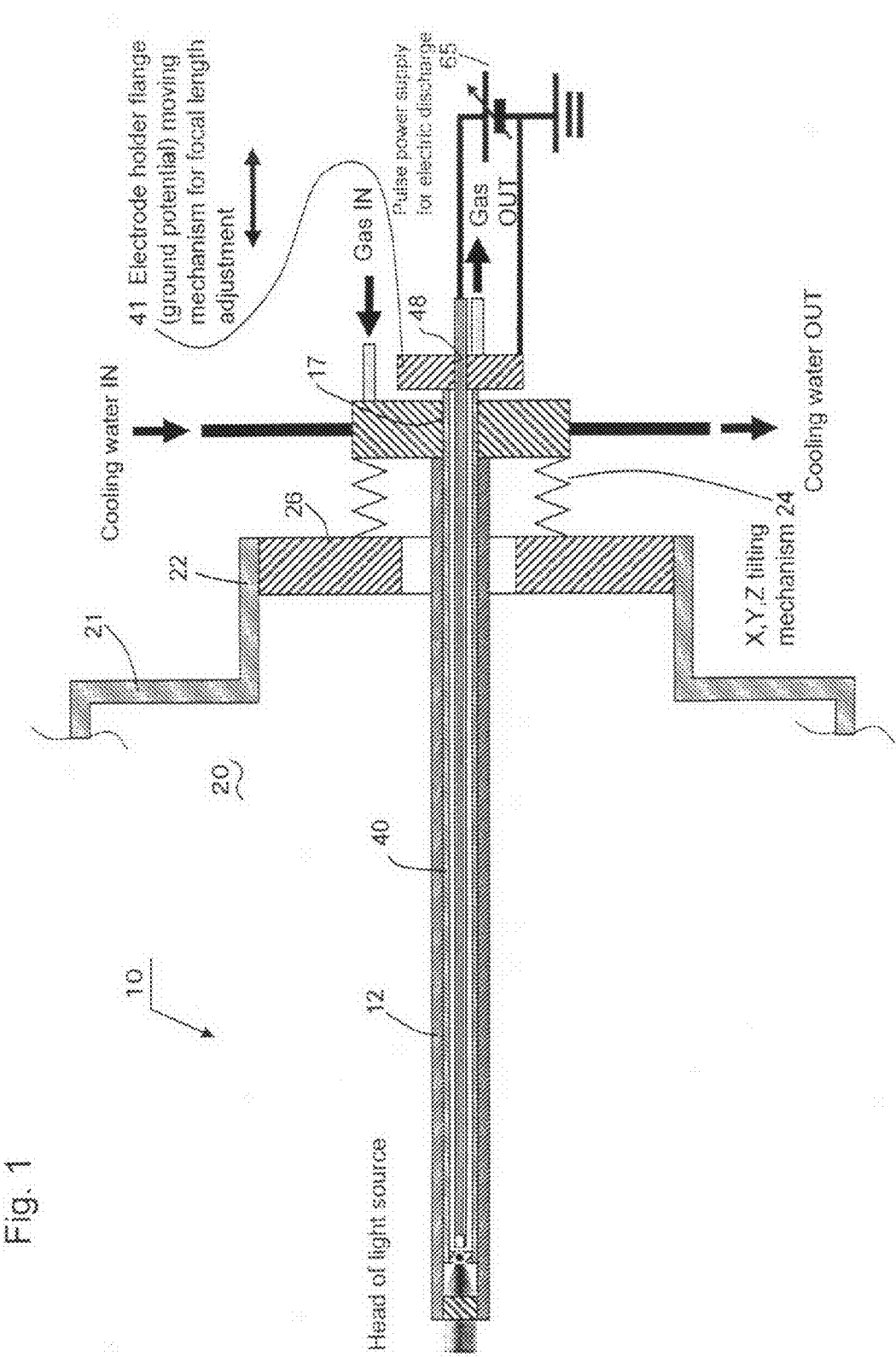
FIG. 1 is a sketch showing the configuration of a light source according to a specific embodiment of the present invention for determining particle density.
Figure 2:
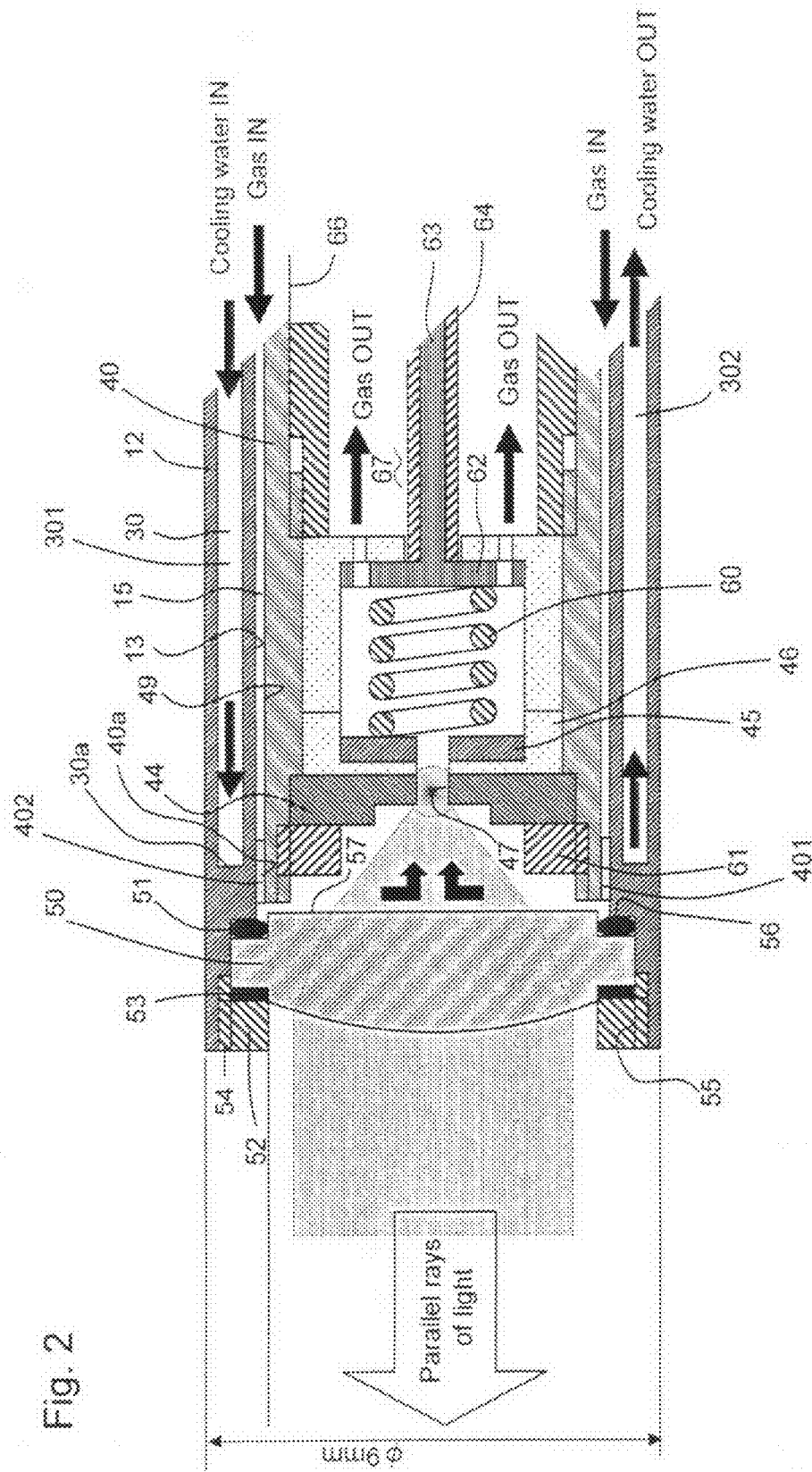
FIG. 2 is an enlarged view of the light source according to the embodiment.

FIG. 1 is a sketch showing the entire configuration of a light source according to Embodiment 1, and FIG. 2 is an enlarged view of the tip end portion (i.e., head) of the light source. The light source 10 according to Embodiment 1 includes a tubular casing 12 (outer diameter: 9 mmφ) made of stainless steel, and the casing 12 has, at its base portion, a flange 14 provided so as to be vertical to the axis of the casing 12. The casing 12 is inserted into a reaction chamber 20 through a window member 26 attached to a port 22 formed on a wall 21 of the reaction chamber 20. The flange 14 of the casing 12 is provided on a well-known XYZ tilting mechanism 24. The XYZ tilting mechanism 24 can move the XYZ coordinates of the tip end of the casing 12 in the reaction chamber 20, and also can tilt the axis of the casing 12 in any direction.

As shown in FIG. 2, a tubular cooling medium passage 30 is formed in the wall of the casing 12 so as to extend along the wall. In the cooling medium passage 30, a partition (not illustrated) is diametrically provided so as to form a supply passage 301 having a semicircular (180°) ring-shaped cross section and a drain passage 302 having a semicircular ring-shaped cross section. The partition axially extends to the vicinity of a bottom portion 30a of the cooling medium passage 30, and the supply passage 301 communicates with the drain passage 302 at the bottom portion 30a. With this configuration, a cooling medium is supplied through the supply passage 301 (toward a lens 50) to the bottom portion 30a of the cooling medium passage 30, and then the cooling medium is returned through the drain passage 302. The cooling medium passage 30 is connected to an inlet 16 and an outlet 18 provided in the flange 14. With this configuration, the cooling medium (water) supplied through the inlet 16 flows through the supply passage 301 of the cooling medium passage 30 toward the tip end of the casing 12, returns through the drain passage 302 of the cooling medium passage 30 toward the flange 14, and is drained through the outlet 18. The casing 12 is cooled by means of circulation of the cooling medium (water). The cooling medium employed may be cooling water, a cooling solvent (e.g., Galden or Fluorinert), or a cooling gas.

Figure 3:
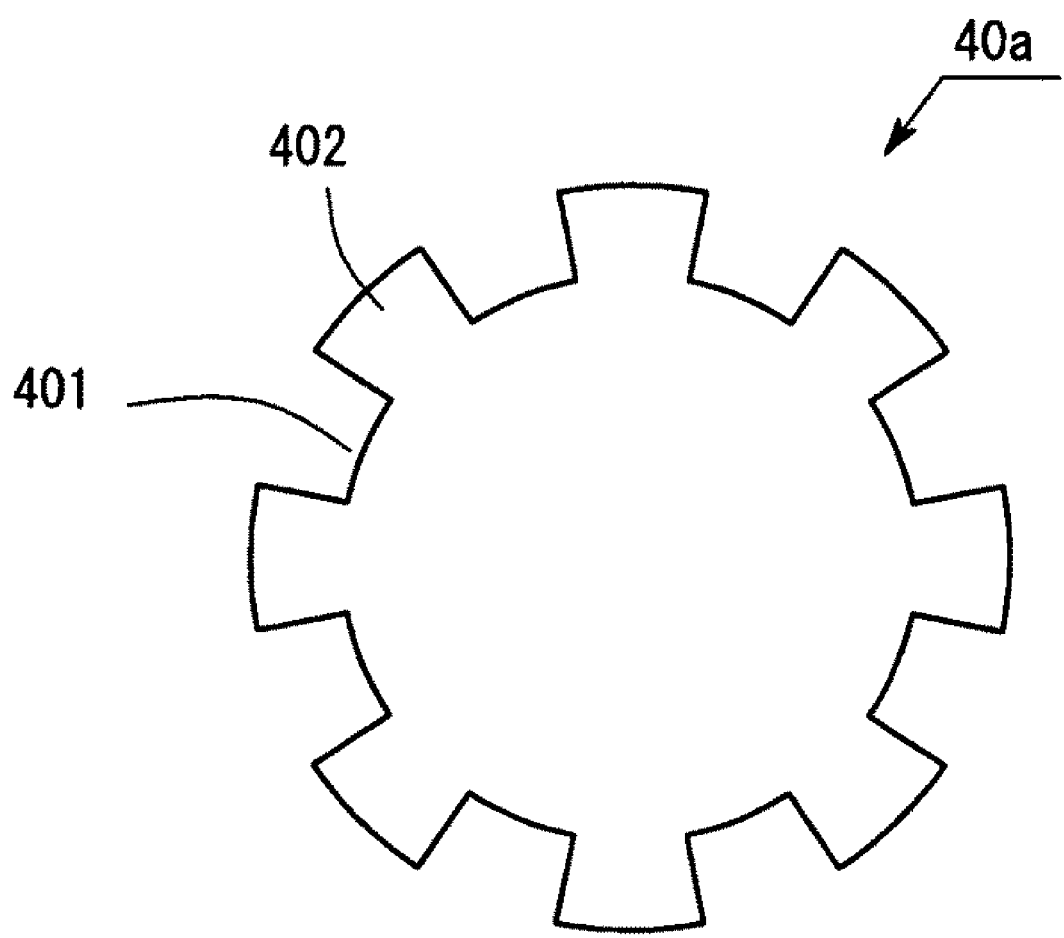
FIG. 3 is a sketch showing the configuration of the tip end of an electrode holder of the light source according to the embodiment.
Figure 4:
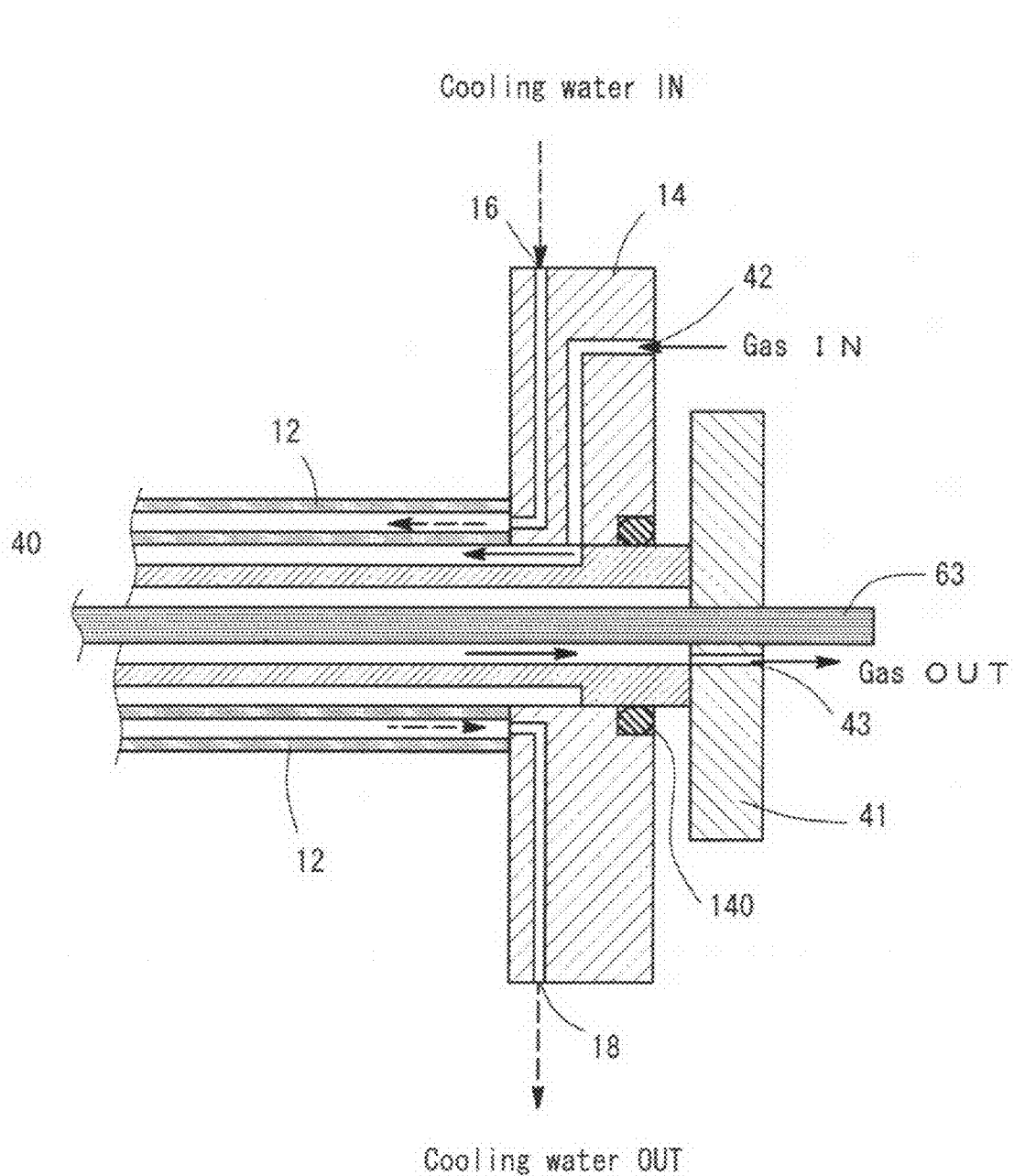
FIG. 4 is a sketch showing the configuration of flanges and the base portion of the electrode holder of the light source according to the embodiment.
Figure 5:
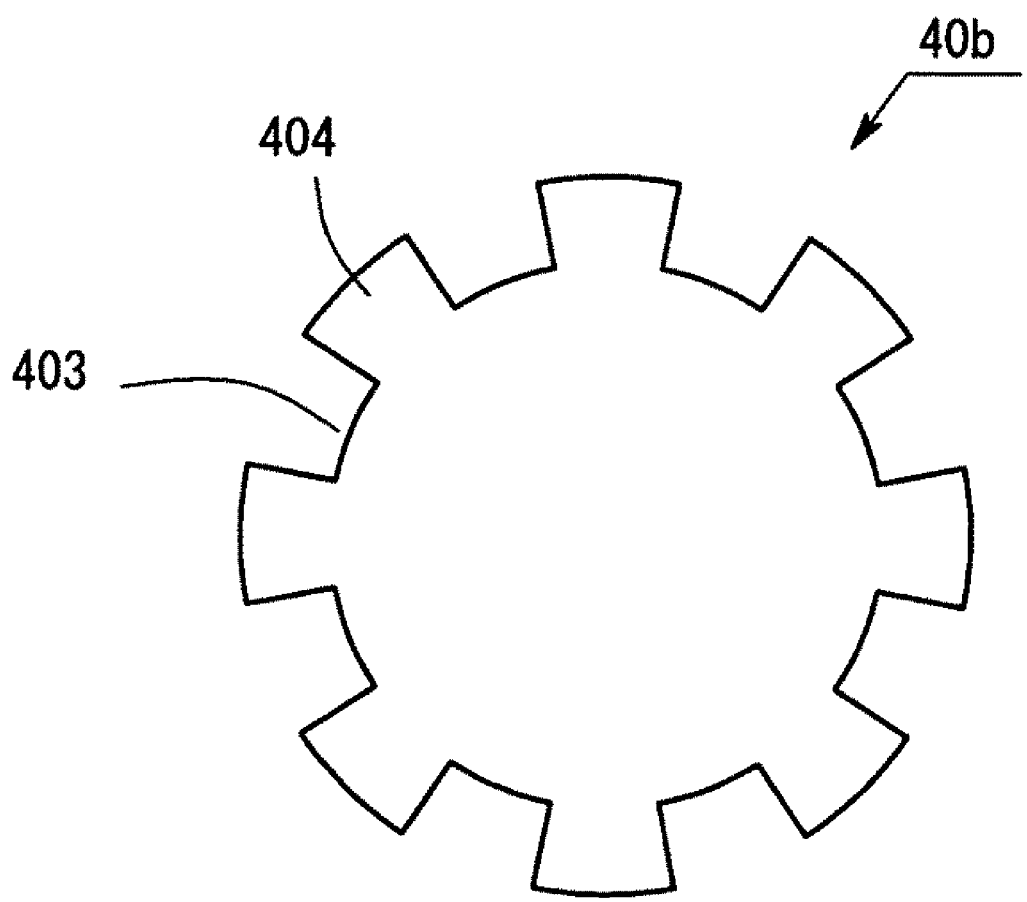
FIG. 5 is a sketch showing the configuration of the base portion of the electrode holder of the light source according to the embodiment.

A tubular electrode holder 40 made of stainless steel is inserted into the casing 12 so as to be movable in an axial direction of the casing 12. The electrode holder 40 has, at its base portion, a flange 41 provided so as to be vertical to the axis of the electrode holder 40. As shown in FIG. 3, the electrode holder 40 has, at its head 40a, eight axially extending protrusions 402, and eight grooves 401 each being formed between adjacent protrusions. The electrode holder 40 is axially slidably held by the casing 12 so that the eight protrusions 402 come into contact with the inner wall 13 of the casing 12. As shown in FIG. 5, the electrode holder 40 has, at its base portion 40b, eight axially extending protrusions 404, and eight grooves 403 each being formed between adjacent protrusions 404. The electrode holder 40 is axially slidably held by the casing 12 so that the eight protrusions 404 abut the inner wall defining a central hole 17 of the flange 14 connected to the casing 12.

An O-ring 140 is provided on a portion (on the side near to the flange 41) of the inner wall defining the central hole 17 of the flange 14. Thus, the electrode holder 40 is axially slidable in the casing 12, with the inside of the casing 12 being kept airtight. A tubular clearance 15 is provided between the outer wall 49 of the electrode holder 40 and the inner wall 13 of the casing 12. The flange 14 has an inlet 42 for supplying an electric discharge gas, and the flange 41 has an outlet 43 for removing the electric discharge gas supplied into the casing 12. An electric discharge gas is supplied through the inlet 141, through the grooves 403 at the base portion 40b of the electrode holder 40, to the aforementioned tubular clearance 15. The electric discharge gas flows through the clearance 15, and is cooled via the inner wall 13 of the casing 12. The clearance 15 serves as a portion of an electric discharge gas passage.

A lens 50 is provided at the tip end of the casing 12. A screw thread 54 is formed on a portion of the inner wall of the tubular casing 12, and a ring-shaped flange 52 having a screw thread 55 formed on its outer wall is screwed into the casing 12 by means of the screw threads 54 and 55. Also, a ring-shaped flange 56 is provided on the casing 12. The lens 50 is placed between the flange 56 and the flange 52 via O-rings 53 and 51 provided on both sides of the lens 50. The lens 50 is fixed to the flange 56 by screwing the flange 52 into the casing 12.

A first electrode 44 serving as a cathode, a second electrode 45 serving as an anode, and a ceramic insulating spacer 46 provided therebetween and having a thickness of 0.2 to 0.5 mm are fixed at the tip end of the electrode holder 40. A communication hole 47 having an inner diameter of 0.1 mmφ to 1 mmφ is provided so as to penetrate the center portions of the first electrode 44, the insulating spacer 46, and the second electrode 45. The tubular electrode holder 40 has a ring-shaped flange 61 fixed at its tip end. The flange 61 is screwed into the inner wall of the tubular electrode holder 40. The first electrode 44, the insulating spacer 46, and the second electrode 45 are biased by means of a coil spring 60 toward the flange 61 and fixed to the flange 61. The end of the coil spring 60 on the side opposite the second electrode 45 is in contact with a plate-shaped flange 62 provided on the tip end of a metallic shaft 63. The metallic shaft 63 is covered with an insulator 64, and the base portion of the metallic shaft 63 penetrates a through-hole 48 of the flange 41 and is fixed to the flange 41. Electric power is supplied from a pulse power supply 65 for electric discharge provided outside the reaction chamber 20 to the metallic shaft 63, and electricity is conducted to the second electrode 45 via the flange 62 and the electrically conductive coil spring 60. The communication hole 47 is connected to the outlet 43 of the flange 41 via an internal space 67 of the electrode holder 40. The space between the lens 50 and the first electrode 44, the communication hole 47, and the space 67 serve as a portion of the electric discharge gas passage.

The light source according to Embodiment 1 is configured as described above. The effects of the light source will next be described. Firstly, cooling water is supplied through the inlet 16 of the flange 14 toward the lens 50 through the supply passage 301 of the cooling medium passage 30 provided in the wall of the casing 12. The cooling water flows through the drain passage 302 of the cooling medium passage 30, and is drained through the outlet 18 of the flange 14. Thus, the casing 12 is cooled by circulating the cooling water through the cooling medium passage 30.

Subsequently, an electric discharge gas is supplied through the inlet 141 of the flange 14, through the eight grooves 403, to the tubular clearance 15 provided between the outer wall 49 of the electrode holder 40 and the inner wall 13 of the casing 12. While the electric discharge gas passes through the tubular clearance 15, the discharge gas is cooled by the inner wall 13 of the casing 12. The thus-cooled electric discharge gas flows toward the back surface 57 of the lens 50 and then flows along the back surface 57 toward the central axis of the casing 12. Thereafter, the electric discharge gas is aspirated through the communication hole 47 provided in the first electrode 44, the insulating spacer 46, and the second electrode 45. Then, the electric discharge gas is aspirated through the space 67 provided between the metallic shaft 63 and the inner wall 66 of the electrode holder 40, and is removed through the outlet 43 of the flange 41. Thus, electric discharge occurs at the communication hole 47 of the first electrode 44. In this case, since the electric discharge gas is cooled, the first electrode 44 and the second electrode 45 are prevented from being abnormally heated. Therefore, electric discharge occurs in a stable manner, and light of constant intensity is emitted. In addition, since the discharge gas flows along the back surface 57 of the lens 50, the back surface 57 is cleaned by the discharge gas, preventing staining of the back surface 57. Also, since the discharge gas flows from the lens 50 toward the first electrode 44, a plasma formed at the communication hole 47 of the first electrode 44 does not flow toward the back surface 57 of the lens 50. Therefore, the back surface 57 of the lens 50 is kept clean, and the lens 50 is prevented from fogging. Thus, light having been passed through the lens 50 exhibits constant intensity, which realizes accurate determination of particle density.

In addition to the aforementioned effect, the light source according to Embodiment 1 exhibits the following effect. The position of the tip end of the casing 12 can be controlled in the reaction chamber 20 by means of the XYZ tilting mechanism 24. Therefore, a spatial distribution profile of particle density in a plasma atmosphere can be accurately obtained by varying the position of the light source. Since the tubular casing 12 has an outer diameter of 9 mmφ, the distribution of particle density can be accurately determined without disturbing the state of a plasma. The casing 12 is cooled by a cooling medium, and thus the first electrode 44, the second electrode 45, the lens 50, the O-rings 51 and 53, and the coil spring 60 are not degraded. Also, the components forming the light source 10 are cooled, and thus thermal expansion is suppressed, whereby assembly accuracy is improved. Since the second electrode 45 is pressed to the insulating spacer 46 by means of the coil spring 60, reliable electrical contact is established between the spring and the electrode, and electric power can be stably supplied to the electrode. Since the electrode holder 40 is axially movable with respect to the casing 12, the distance between the lens 50 and the first electrode 44 can be adjusted. Therefore, the distance can be optimized for a target emission wavelength, and parallel rays of light can be obtained with high accuracy, even the emission wavelength is modified. For determination of the hydrogen radical density, oxygen radical density, or nitrogen radical density, hydrogen gas, oxygen gas, or nitrogen gas is respectively employed as an electric discharge gas. The light source according to Embodiment 1 can be employed in common for these electric discharge gases, even when light of different wavelengths is emitted by electric discharge of these gases.

Since the thin ceramic insulating spacer 46 is provided between the first electrode 44 and the second electrode 45, abnormal electric discharge between the electrodes can be prevented, and consumption of the electrodes can be reduced. The first electrode 44 can be parallelized to the second electrode 45 with high accuracy by means of the insulating spacer 46, and thus reliable electric discharge is achieved. In addition, when the thickness of the insulating spacer 46 is optimized for, for example, an electric discharge gas employed, reliable electric discharge is realized, and light of constant intensity can be obtained. When the width of the first electrode 44 is reduced to about 1 mm at a position in the vicinity of the communication hole 47, and increased to about 2 mm at a position radially before the axis of the casing, the luminance of light emitted can be increased, and the heat radiation property of the first electrode 44 can be improved.

When the first electrode 44 and the second electrode 45 are formed from oxygen-free copper, a plasma serving as an emission source is prevented from being contaminated with impurities. Therefore, pure emission of desired wavelength can be obtained, and good heat radiation property is attained. Since an emission source is located at the head of the casing 12, even when the position of the casing 12 is varied in the reaction chamber 20, emission of constant intensity can be obtained, and a spatial distribution profile of particle density can be accurately obtained. Since a stepped lens is employed as the lens 50, assembly accuracy can be improved. When the components of the light source 10 according to Embodiment 1 are baked in vacuo before being assembled, release of impurity gases from these components can be prevented, and an optically pure emission spectrum can be obtained.

INDUSTRIAL APPLICABILITY

The present invention can be applied to accurate determination of the particle density of a plasma atmosphere for performing, with high accuracy, film formation or etching by means of a plasma processing apparatus or a plasma.

The invention claimed is:

1. A light source which, when in use, is inserted into a reaction chamber for generating a plasma atmosphere, and which is employed for determining an atom or a molecule density of the plasma atmosphere through an absorption spectroscopy, said light source comprising:
   a tubular casing comprising a base portion and tip end;
   a cooling medium passage for causing a cooling medium to flow therethrough, the passage being provided along an inner wall of the casing and comprising a supply passage extending from the base portion to a bottom portion disposed near the tip end and a drain passage extending from the bottom portion to the base portion, the supply passage communicating with the drain passage at the bottom portion;
   a lens provided at the tip end of the casing;
   a first electrode and a second electrode which are provided in the casing and before the lens so as to be vertical to an axis of the casing and parallel to each other;
   an insulating spacer provided between the first electrode and the second electrode;
   a hole axially penetrating center portions of the first electrode, the insulating spacer, and the second electrode; and
   an electric discharge gas passage for introducing an electric discharge gas, along an inner wall of the cooling medium passage, to a back surface of the lens so that the electric discharge gas is reflected by the lens and flows through the hole in a direction of the base portion.

2. A light source according to claim 1, wherein the light source further includes an electrically conductive spring for pressing the second electrode to the insulating spacer, and
   wherein a voltage is applied to the second electrode via the spring.

3. A light source according to claim 2, wherein the light source further includes a tubular electrode holder which is axially movably provided in the casing so as to support the first electrode, the insulating spacer, and the second electrode, and to be parallel to the axis of the casing, so that a clearance is provided between an outer wall of the electrode holder and the inner wall of the cooling medium passage and
   wherein the clearance and an internal space of the electrode holder serve as the electric discharge gas passage.

4. A light source according to claim 1, wherein the light source further includes a tubular electrode holder which is axially movably provided in the casing so as to support the first electrode, the insulating spacer, and the second electrode, and to be parallel to the axis of the casing, so that a clearance is provided between an outer wall of the electrode holder and the inner wall of the cooling medium passage and
   wherein the clearance and an internal space of the electrode holder serve as the electric discharge gas passage.

5. A light source according to claim 1, wherein a plasma is formed in a space between the first electrode and the second electrode.

6. A light source according to claim 1, wherein a plasma is formed in the hole at the first electrode.

7. A light source according to claim 1, further comprising:
   an electrode holder inserted into the casing and being movable in an axial direction of the casing to adjust a distance between the first electrode and the lens.

8. A light source according to claim 1, wherein the first electrode comprises a cathode and the second electrode comprises an anode.

9. A light source according to claim 1, further comprising:
   a flange facing the second electrode; and
   an electrically conductive spring attached to the flange and the second electrode for pressing the second electrode to the insulating spacer.

10. A light source according to claim 9, further comprising:
    a power supply for providing an electric discharge from an outside of the reaction chamber to the second electrode via the flange and the electrically conductive spring.

11. A light source according to claim 1, wherein the electric discharge gas passage comprises a space between the lens, the first electrode, and the hole.

12. A light source according to claim 1, wherein the electric discharge gas is aspirated through the hole provided in the first electrode, the insulating spacer, and the second electrode.

* * * * *